United States Patent
Zelechonok et al.

(10) Patent No.: US 7,862,716 B2
(45) Date of Patent: Jan. 4, 2011

(54) HPLC SCHEMATIC WITH INTEGRATED SAMPLE CLEANING SYSTEM

(75) Inventors: Yury Zelechonok, Northbrook, IL (US); Vladislav Orlovsky, Wheeling, IL (US)

(73) Assignee: SIELC Technologies Corporation, Prospect Heights, IL (US)

( * ) Notice: Subject to any disclaimer, the term of this patent is extended or adjusted under 35 U.S.C. 154(b) by 142 days.

(21) Appl. No.: 12/384,994

(22) Filed: Apr. 13, 2009

(65) Prior Publication Data
US 2010/0258487 A1    Oct. 14, 2010

(51) Int. Cl.
*B01D 15/08* (2006.01)

(52) U.S. Cl. .................... 210/198.2; 210/656; 210/659; 210/143

(58) Field of Classification Search .............. 210/635, 210/656, 659, 96.1, 143, 198.2; 96/101, 96/103
See application file for complete search history.

(56) References Cited

U.S. PATENT DOCUMENTS

| | | | | |
|---|---|---|---|---|
| 4,577,492 A * | 3/1986 | Holba et al. | .............. | 73/61.53 |
| 5,011,608 A * | 4/1991 | Damjanovic | .............. | 210/656 |
| 5,071,547 A * | 12/1991 | Cazer et al. | .............. | 210/198.2 |
| 5,547,497 A * | 8/1996 | Klemp et al. | .............. | 96/104 |
| 5,652,398 A * | 7/1997 | Johnson | .............. | 73/863.71 |
| 5,922,754 A * | 7/1999 | Burchett et al. | .............. | 514/449 |
| 5,933,357 A * | 8/1999 | Tipler | .............. | 700/273 |
| 5,983,703 A * | 11/1999 | Wylie et al. | .............. | 73/23.42 |
| 6,952,946 B2 * | 10/2005 | Mueller | .............. | 73/23.4 |
| 2003/0124680 A1* | 7/2003 | Reeves et al. | .............. | 435/76 |
| 2004/0087003 A1* | 5/2004 | Hu et al. | .............. | 435/252.33 |
| 2004/0099046 A1* | 5/2004 | Mueller | .............. | 73/23.4 |
| 2009/0208365 A1* | 8/2009 | McSherry et al. | .............. | 422/2 |

* cited by examiner

*Primary Examiner*—Ernest G Therkorn
(74) *Attorney, Agent, or Firm*—John C. Shepard; Charles F. Lind

(57) ABSTRACT

The disclosed HPLC flow schematic back-flushes the guard column with mobile phase once every operating cycle, the regular cleaning maintaining its effectiveness and useful life. This mobile phase flow reversal is accomplished by imposing a two position multiple port switching valve between the guard and separation columns. In one valve position, the mobile phase is pumped in one flow direction through both the separation and guard columns, but the switched valve maintains the same flow direction only through the separation column and reverses the mobile phase flow direction through the guard column, for effectively cleaning the guard column. Moreover, the mobile phase back flow is directed over the emptied sample drawing needle for cleaning it to reduce possible sample cross contamination. The improved flow circuits use basically only the typical HPLC system components, except for some insignificant modifications from existing injector designs.

12 Claims, 3 Drawing Sheets

HPLC SCHEMATIC WITH INTEGRATED SAMPLE CLEANING SYSTEM

FIELD OF THE INVENTION

This invention relates to high performance liquid chromatography (HPLC), and more specifically to a flow circuit arrangement employed for improved operation of HPLC analysis of complex matrix samples and for improved control of sample carryover.

BACKGROUND OF THE INVENTION

HPLC technology is widely used to detect and identify different components contained in a test sample. Typical HPLC instruments use a high pressure pump for forcing a suitable mobile phase, via capillary lines, at a constant flow rate serially through an autosampler, a separation column and a UV or other type detector. The column contains an absorbent selected for the components anticipated to be in the test samples. For instigating a run, a small quantity of the test sample is introduced into the mobile phase by an injector to travel through the separation column. The different sub phase sample components pass through the column at different rates, each thereby becoming substantially isolated before passing the detector for individual identification.

When test samples include undesirable matrices, the sample needs to be cleaned. The usual way of cleaning involves filtration, centrifugation, precipitation, or absorption of matrices prior to the introduction of the sample into the HPLC system. Alternatively, the direct way to achieve cleaning is to include in the HPLC flow schematic a guard column located upstream of the separation column, operable to trap out matrices from flowing into and blocking the separation column, which would dramatically shorten its useful separation life. The guard column is inexpensive compared to the separation column, and is expected to be replaced frequently. However, replacement of the guard column is not without significance, as it must include both the cost of the new guard column and the down time of the HPLC system while installing it.

OBJECTS, FEATURE AND SUMMARY OF THE INVENTION

A basic object of this invention is to provide in an HPLC flow arrangement having the same basic components as common HPLC systems, but further allowing for regularly back flushing of the guard column with mobile phase, to clean it and extend its useful life of preventing any flow system matrix from reaching the more costly downstream separation column.

A more specific object of this invention is to provide means for automatically and frequently backflushing the HPLC system guard column with the mobile phase, for regenerating or improving the guard column for yielding its reliable protection of the separation column, even over repeated operational cycles.

Another object of this invention is to provide an HPLC system having a washing means for cleaning the injector needle, the sample loop, and connecting lines after each sample injection, for minimizing sample carryover in the system.

Still another object of this invention is to eliminate the need for a purge valve and its operation for manually purging air trapped in the high pressure pump head, as the improved flow circuit and high pressure syringe used in the flow schematic can be operated to provide the same purging action.

BRIEF DESCRIPTION OF THE DRAWINGS

These and other objects, features or advantages of the invention will be more fully understood and appreciated after considering the following disclosure of the invention, which includes the accompanying drawings, wherein.

DETAILED DESCRIPTION OF THE INVENTION

Figure 1:
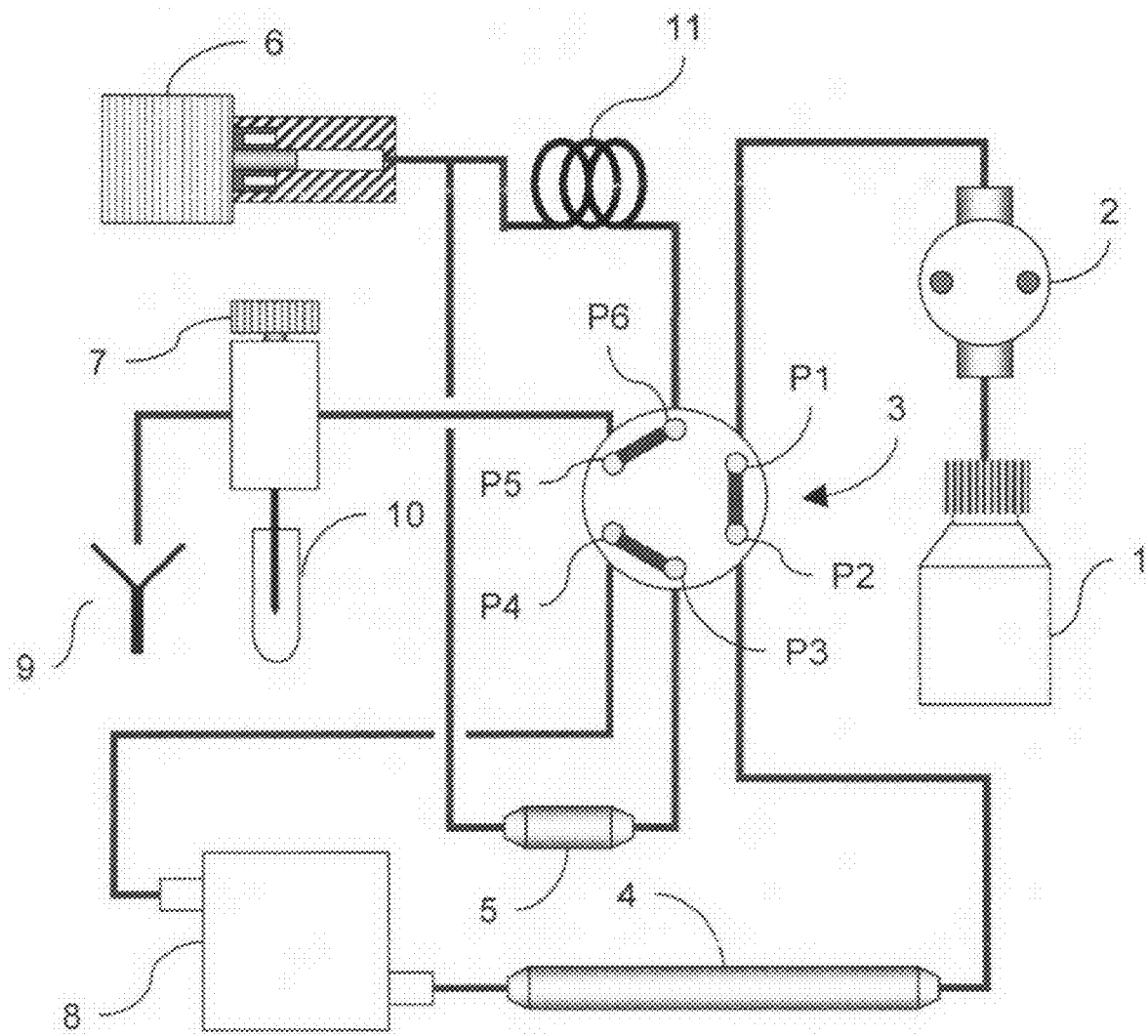
FIG. 1 illustrates the improved HPLC flow schematic in a first operational valve position where the syringe will draw sample from the sample container and into the HPLC flow lines.

The disclosed HPLC schematic has a mobile phase vessel 1, a high pressure pump 2, a two position six-port valve 3, a separation column 4, a guard column 5, a syringe 6 for drawing the sample, an injector 7 having a needle 18 to draw the liquid sample from the container 10, a detector 8, a waste outlet 9 for the used mobile phase, and a sample accumulation loop 11.

More specifically, the six-port valve 3 has permanent line connections as follows: port P1 to the outlet of pump 2; port P2 to the inlet of separation column 4; port P3 to one end of guard column 5; port P4 to the outlet of detector 8; port P5 through ports of the injector 7 to waste line 9; and port P6 is via accumulation loop 11 to the syringe 6 and the other end of the guard column 5.

The valve 3 shifts between two operative positions: FIGS. 1 and 3 illustrating one position where ports P1 and P2, ports P3 and P4, and P5 and P6 are respectively connected; and FIG. 2 illustrating the other operative position where ports P2 and P3, ports P4 and P5, and P6 and P1 are respectively connected.

In FIG. 1, the valve 3 is positioned to fill the accumulation loop 11 with the sample, whereby powered actuation of the syringe draws sample from the container 10 via the injector needle 18, and the connected ports P5 and P6.

Figure 2:
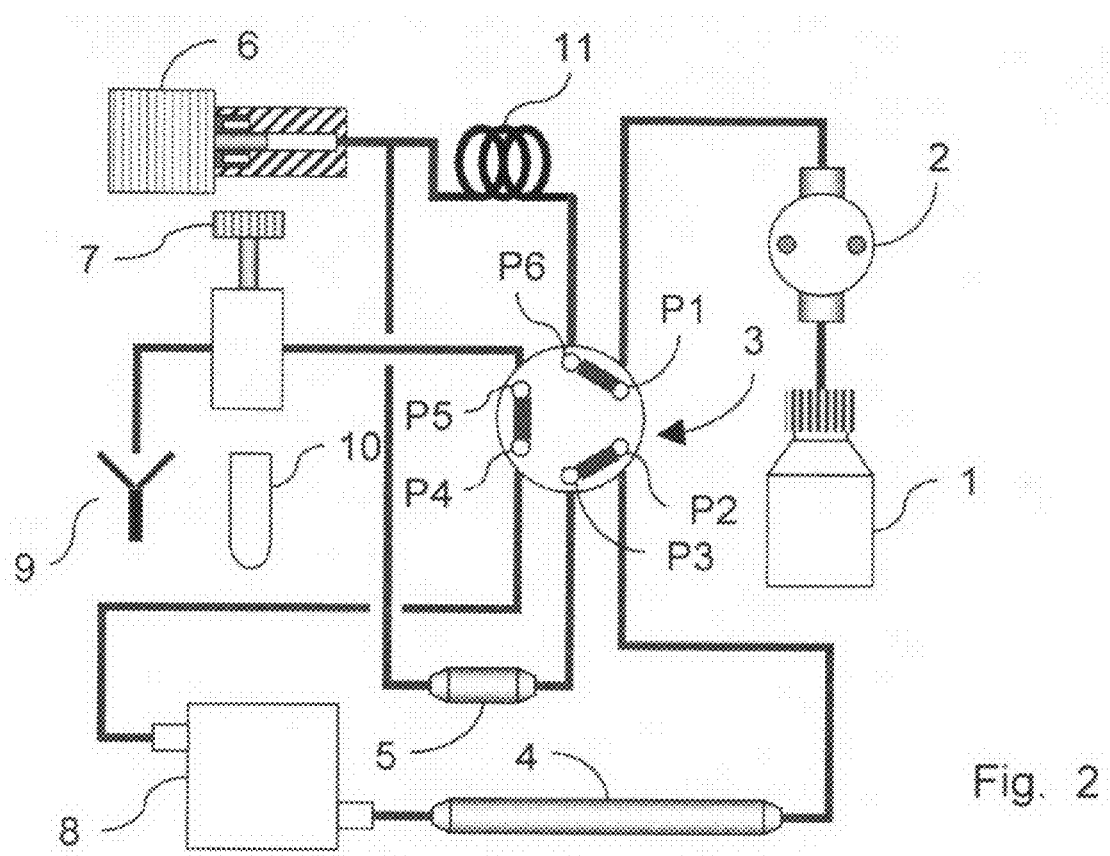
FIG. 2 illustrates the HPLC flow schematic in a second operational valve position where the sample and mobile phase are pumped through the guard and separation columns.
Figure 3:
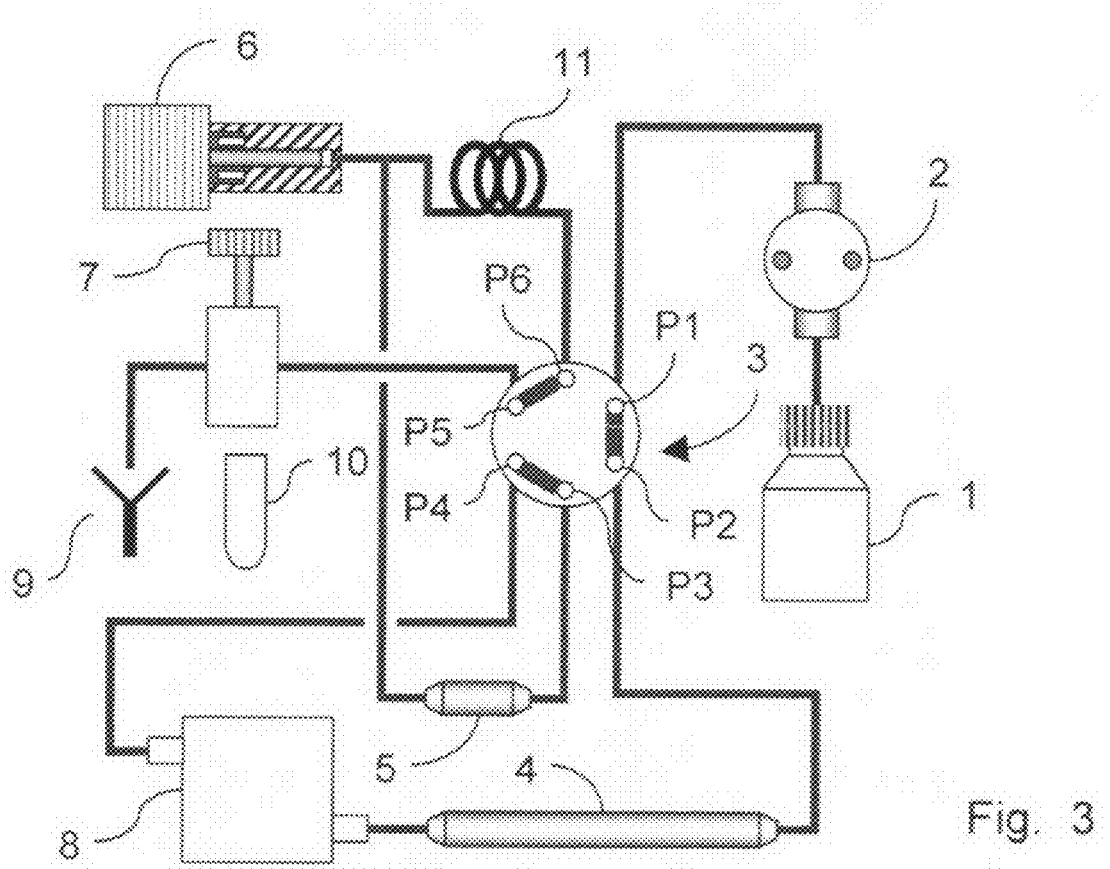
FIG. 3 illustrates the inventive HPLC flow schematic in the first operational valve position again where the mobile phase is back-flushed through the guard column, serving to clean it.

The FIG. 2 flow schematic provides for the sample to travel via connected ports P1 and P6, P2 and P3, and P4 and P5 throughout the flow lines; where pump 2 operation powers the mobile phase sequentially through the sample accumulation loop 11, the guard column 5, the separation column 4, the detector 8, and via the injector 7 to waste 9. It is during this cycle that the guard column 5 isolates the undesired sample matrix components from the desired analytes flowing to the separation column 4. The desired sample analytes then flow sequentially through the separation column 4, the detector 8, and the injector 7 into the waste to be discharged.

FIG. 3 provides the inventive guard column flushing cycle, via connected ports P1 and P2, P3 and P4, and P5 and P6 that directs the mobile phase from the pump through the separation column 4 and detector 8 in the same direction as in the FIG. 2 flow schematic; but via connected ports P3 and P4 reverses the mobile phase flow direction through the guard column 5 and accumulation loop 11, and past the syringe 6, for discharge to the waste 9 via connected ports P5 and P6. This valve setting also allows the syringe 6 to be emptied, with its contents being carried with the mobile phase into the waste.

After this back flow cycle of FIG. 3 is completed, the pump 2 is stopped, with the component connections arranged to begin the cycle operation of FIG. 1 again, after a new sample might be drawn by the injector 7 from sample container 10.

It is during the cycles of FIGS. 2 and 3 that sample analytes travel through the column 4, become separated, and are identified in the detector 8.

The FIG. 3, the mobile phase back flows through and effectively flushes the guard column 5 clean, for enhancing its reliable performance of protecting the separation column, and extending its useful operational life. As this cleaning is automatic once every operating cycle, the cleaned guard column substantially reduces the possibility of the separation column becoming clogged and ineffective.

Figures 4, 5:
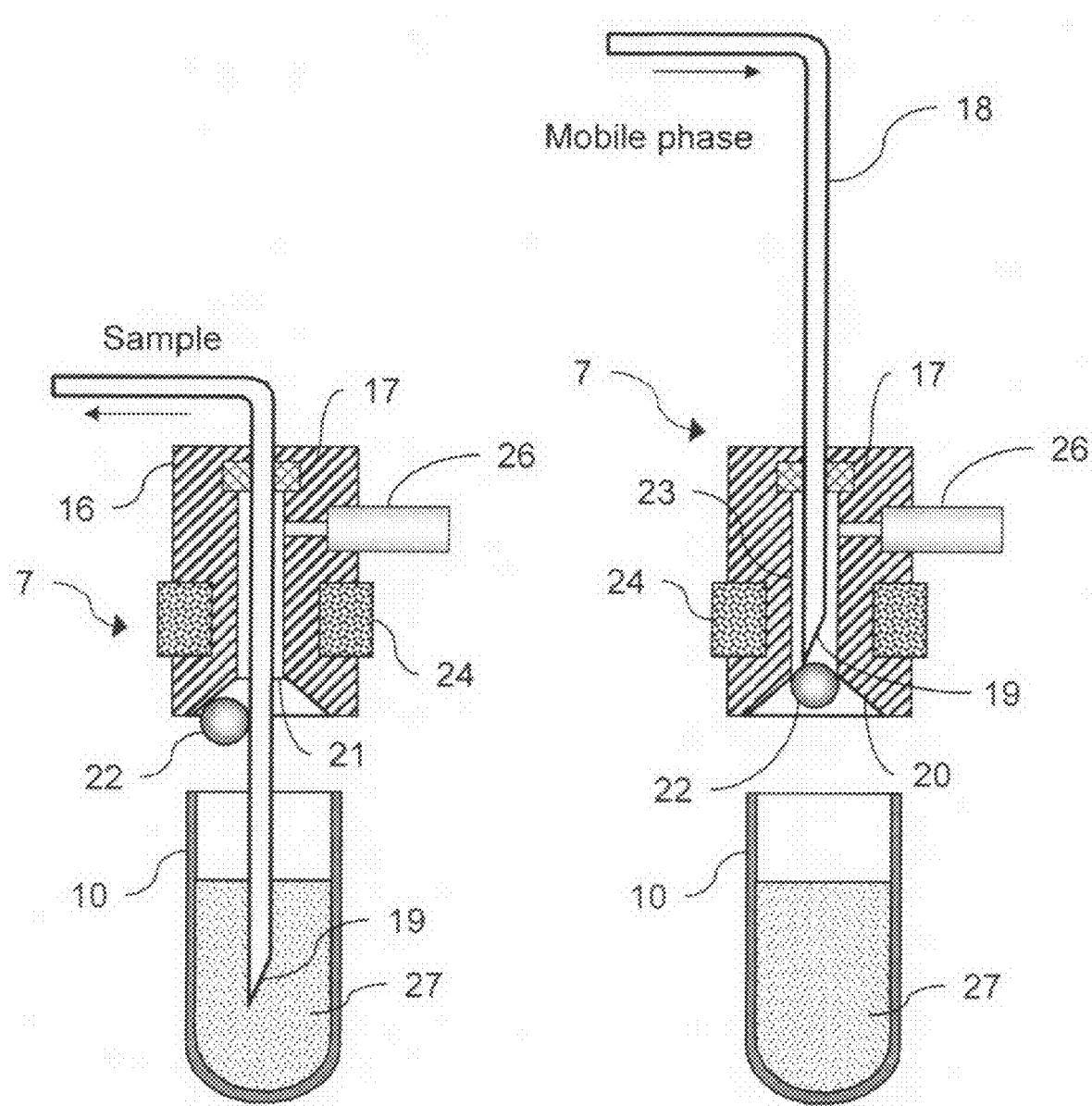
FIG. 4 is a sectional view of a injector used in the flow circuit of FIGS. 1-3, with the needle submerged in the sample container for drawing sample into the flow circuit.
FIG. 5 is a sectional view of the injector of FIG. 4, except with the needle withdrawn from the sample and positioned in an enclosure for washing residue sample off it.

FIGS. 4 and 5 illustrate details of the injector 7 and its cooperation with the sample container 10, as already identified in the HPLC system of FIGS. 1, 2 and 3.

The injector 7 includes a housing 16 having a bore 23 with an annular top seal 17 that surrounds needle 18. The needle 18 is adapted to be shifted axially in the housing 16 between lowered and raised positions. In its lowered position (FIG. 4), the open tip 19 of the needle is submerged in the liquid sample held isn an underlying vessel, while in its raised position (see FIG. 5), the tip is elevated above both the liquid sample and the housing bore outlet 21. Further, a ball 22 is biased upwardly against conical seat 20 effective to close needle housing outlet 21 from the bore 23. The ball 22 can be of a magnet responsive material, and a magnet 24 can be located in the needle housing above the seat 20, operable to attract and hold the ball against the seat and over the house outlet 21, to close the bore passage 23.

With the needle 18 in the passage 23 and the ball closing the passage outlet, mobile phase conveyed into the bore cavity 23 (see FIGS. 3 and 5) via the needle, will flow over and wash the needle tip and will then be discharged via line 26 to the waste 9. This needle washing cycle removes sample residual on the needle, for reducing possible sample cross-contamination.

The needle 18 can also be shifted downwardly, to shift the ball 22 out of the way and then be inserted into the liquid sample (see FIGS. 1 and 5) in the container 10. As so positioned, suction applied by the syringe 6 will effectively draw the sample into the loop 11.

Another useful and unexpected aspect of the disclosed system is that it can remove air trapped in the pump 2. Thus, the pump typically has a very small volume cycle displacement, and possibly an air bubble therein can preclude initial startup. To remove the air bubble before pump startup, the syringe 6 can be operated to draws the contents from the pump 2, whereupon the valve 3 can then be shifted and the syringe reversed to discharge syringe content to the waste. This cycle can be repeated one or more times to achieve reliable initial pump operation.

While the invention has been illustrated and disclosed specifically, minor changes could be made without departing from the inventive concepts. Accordingly, the invention is to be limited only by the following claims.

What is claimed is:

1. An HPLC flow system, comprising
   a separation column; a detector; and means connecting the outlet end of the separation column with the detector;
   a syringe; an injector with a sample reservoir; a sample accumulation loop; a guard column; and means connecting the syringe to the accumulation loop, to one end of the guard column, and to the injector, sample reservoir and waste; and
   a mobile phase reservoir; a high pressure pump; and valve means operable:
      in a first operative position to define a first flow schematic serially connecting the injector and sample reservoir, accumulation loop, and syringe, whereby powered syringe intake draws the sample into the accumulation loop; and
      in a second operative position to define a second flow schematic serially connecting the pump, accumulation loop, guard column, separation column, detector, and the injector to waste, whereby pump operation advances the mobile phase and sample in one direction serially through these components; and
      in the first operative position again to define a third flow schematic, whereby pump operation advances the mobile phase in the same direction through the separation column and detector, while advancing the mobile phase in the reverse direction through the guard column for back flushing it.

2. An HPLC flow system according to claim 1, with the pump operation in the third flow schematic, also advancing the mobile phase in the reverse washing direction through the accumulation loop and injector to waste.

3. An HPLC flow system according to claim 1, wherein the valve means is comprised as a six-port valve having two operative positions selectively connecting three paired ports respectively in each operative position.

4. An HPLC flow system according to claim 3, wherein the valve means port 1P is connected to the pump outlet, port 2P is connected to the separation column inlet, port 3P is connected to one guard column end, port 4P is connected to the detector outlet, port 5P is connected to the sample reservoir, and port 6P is connected via the accumulation loop to the syringe.

5. An HPLC flow system according to claim 4, where the first operative valve position operatively connect the ports 1P and 2P, the ports 3P and 4P, and the ports 5P and 6P; and where the second operative valve position operatively connect the ports 2P and 3P, the ports 4P and 5P, and the ports 6P and 1P.

6. An HPLC flow system according to claim 5, where the syringe is connected via the six-port two position valve to the high pressure pump, operable when initially operated to purge air trapped in the pump, allowing initial pump operation to effectively pump the mobile phase.

7. An HPLC flow system according to claim 1, further including an injector with a needle having an inlet/outlet open tip adapted during the defined first flow schematic to be inserted into the sample reservoir and adapted during the defined second and third flow schematics to be positioned outside of the sample reservoir; and means operable in the defined second and third flow schematics to discharge mobile phase from the needle for washing residual sample therefrom.

8. An HPLC flow system according to claim 1, further including a housing having a bore with an open lower end, a seal at the bore upper end surrounding and sealing the needle relative to the bore while said needle otherwise fits with annular clearance between it and the housing bore, said needle mounting allowing said needle to be shifted axially between a lowered position having its tip outside of the bore and submerged in the sample and a raised positions having its tip out of the sample and fitted within the bore, means to close the lower bore end with the needle tip within the bore, outlet means from the bore to the waste, and means for directing mobile phase discharged from the needle into the bore and over the needle for washing sample residual thereon and discharge then via the outlet means to the waste.

9. An HPLC flow schematic according to claim 8, further with the housing having a conical seat expanding downwardly from the lower end of the bore, a ball suited to fit against the seat and close the lower bore end, a magnet located in the needle housing above the seat, and said ball being formed of a magnet responsive material operable to be attracted against the seat and over the lower open bore end, operable as said means for closing the lower bore end.

10. An HPLC flow schematic according to claim 9, further where downward shifting of the needle first disengages the ball from the seat and then allows the needle open tip to be inserted into the underlying liquid sample for drawing sample into the needle.

11. An HPLC flow system according to claim 10, where the syringe is connected via the six-port two position valve to the high pressure pump, operable when initially operated to purge air trapped in the pump, allowing initial pump operation to effectively pump the mobile phase.

12. An HPLC flow system according to claim 11, further including an injector with a needle having an inlet/outlet open tip adapted during the defined first flow schematic to be inserted into the sample reservoir and adapted during the defined second and third flow schematics to be positioned outside of the sample reservoir; and means operable in the defined second and third flow schematics to discharge mobile phase from the needle for washing residual sample therefrom.

* * * * *